US00PP21102P2

(12) United States Plant Patent
Takahata et al.

(10) Patent No.: US PP21,102 P2
(45) Date of Patent: Jun. 29, 2010

(54) ***IPOMOEA* PLANT NAMED 'KYUIKUKAN 5'**

(50) Latin Name: *Ipomoea batatas*
Varietal Denomination: Kyuikukan 5

(75) Inventors: Yasuhiro Takahata, Miyakonojo (JP); Masaru Yoshinaga, Miyakonojo (JP); Hiroki Nakayama, Miyakonojo (JP); Masaru Tanaka, Miyakonojo (JP); Yoshinori Nakazawa, Kumamoto (JP); Toru Kumagai, Tsukuba (JP); Yumi Kai, Miyakonojo (JP); Kenji Katayama, Miyakonojo (JP); Tetsufumi Sakai, Miyakonojo (JP); Kazunari Iwaki, Kanagawa (JP); Yasuyuki Murakami, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/383,282

(22) Filed: Mar. 23, 2009

(51) Int. Cl.
*A01H 5/00* (2006.01)

(52) U.S. Cl. ..... Plt./258

(58) Field of Classification Search ..... Plt./258
See application file for complete search history.

*Primary Examiner*—Susan B McCormick Ewoldt
(74) *Attorney, Agent, or Firm*—C. A. Whealy

(57) ABSTRACT

A new and distinct cultivar of *Ipomoea* plant named 'Kyuikukan 5', characterized by its compact and trailing growth habit and cordate-shaped leaves that are light green when developing and becoming dark purple with further development.

2 Drawing Sheets

Botanical designation: *Ipomoea batatas*.
Cultivar denomination: 'KYUIKUKAN 5'.

BACKGROUND OF THE INVENTION

The present invention relates to a new and distinct cultivar of *Ipomoea* plant, botanically known as *Ipomoea batatas*, and hereinafter referred to by the name 'Kyuikukan 5'.

The new *Ipomoea* plant is a product of a planned breeding program conducted by the Inventors in Miyazaki, Japan. The objective of the breeding program is to create new compact, freely branching trailing-type *Ipomoea* cultivars with attractive foliage shape and coloration.

The new *Ipomoea* plant originated from an open-pollination made by the Inventors in June, 2001 of a proprietary selection of *Ipomoea batatas* identified as code number KOP99205-1, not patented, as the female, or seed, parent with an unknown selection of *Ipomoea batatas* as the male, or pollen, parent. The new *Ipomoea* was discovered and selected by the Inventors as a single plant within the progeny of the stated open-pollination in a controlled greenhouse environment in Miyazaki, Japan in 2001.

Asexual reproduction of the new *Ipomoea* by terminal cuttings in a controlled greenhouse environment in Miyazaki, Japan since the spring of 2002, has shown that the unique features of this new *Ipomoea* plant are stable and reproduced true to type in successive generations.

SUMMARY OF THE INVENTION

Plants of the new *Ipomoea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Kyuikukan 5'.

These characteristics in combination distinguish 'Kyuikukan 5' as a new and distinct cultivar of *Ipomoea:*

1. Compact and trailing growth habit.
2. Cordate-shaped leaves that are light green when developing and becoming dark purple with further development.

Plants of the new *Ipomoea* can be compared to plants of the female parent selection. Plants of the new *Ipomoea* differ from plants of the female parent selection primarily in plant size as plants of the new *Ipomoea* are more compact and have shorter internodes than plants of the female parent selection.

Plants of the new *Ipomoea* can be compared to plants of the *Ipomoea batatas* 'Sweet Caroline Purple', disclosed in U.S. Plant Pat. No. 14,912. In side-by-side comparisons conducted in Shiga, Japan, plants of the new *Ipomoea* differed from plants of 'Sweet Caroline Purple' in the following characteristics:

1. Plants of the new *Ipomoea* were more compact and more trialing than plants of 'Sweet Caroline Purple'.
2. Plants of the new *Ipomoea* and 'Sweet Caroline Purple' differed in leaf shape as plants of 'Sweet Caroline Purple' had palmate-shaped leaves.

BRIEF DESCRIPTION OF THE PHOTOGRAPHS

The accompanying colored photographs illustrate the overall appearance of the new *Ipomoea*, showing the colors as true as it is reasonably possible to obtain in colored reproductions of this type. Colors in the photographs may differ slightly from the color values cited in the detailed botanical description which accurately describe the colors of the new *Ipomoea* plant.

The photograph on the first sheet comprises a side perspective view of typical plants of 'Kyuikukan 5'.

The photograph at the top of the second sheet comprises a close-up view of typical leaves of 'Kyuikukan 5'.

The photograph at the bottom of the second sheet is a close-up view of typical tubers of 'Kyuikukan 5'.

DETAILED BOTANICAL DESCRIPTION

The aforementioned photographs and following observations, measurements and values describe plants grown in Shiga, Japan in an outdoor nursery during the summer and under conditions which closely approximate commercial *Ipomoea* production. During the production of the plants, average day temperatures were 23° C. and average night temperatures were 13° C. Plants were about five months old when the photographs and description were taken. In the detailed description, color references are made to The Royal Horticultural Society Colour Chart, 2001 Edition, except where general terms of ordinary dictionary significance are used.

Botanical classification: *Ipomoea batatas* 'Kyuikukan 5'.

Parentage:

*Female, or seed, parent.*—Proprietary selection of *Ipomoea batatas* identified as code number KOP99205-1, not patented.

*Male, or pollen, parent.*—Unknown selection of *Ipomoea batatas*, not patented.

Propagation:

*Type.*—By terminal cuttings.

*Time to initiate roots.*—About three days at temperatures of 20° C. to 25° C.

*Time to produce a rooted young plant.*—About four weeks at temperatures of 20° C. to 25° C.

*Root description.*—Thick, fleshy, white in color.

*Tuber description.*—Ellipsoidal in shape and whitish in color.

Plant description:

*Plant habit.*—Compact and trailing plant habit; freely branching habit; pinching enhances lateral branch development; vigorous growth habit.

*Plant height.*—About 12.4 cm.

*Plant diameter.*—About 39 cm.

Lateral branch description:

*Length.*—About 22.8 cm.

*Diameter.*—About 4.3 mm.

*Internode length.*—About 1.3 cm.

*Strength.*—Strong.

*Texture.*—Pubescent.

*Color.*—Close to 187A.

Foliage description:

*Arrangement.*—Alternate, simple.

*Length.*—About 11 cm.

*Width.*—About 9 cm.

*Shape.*—Cordate.

*Apex.*—Acute.

*Base.*—Cordate.

*Margin.*—Entire.

*Texture, upper and lower surfaces.*—Sparsely pubescent.

*Venation pattern.*—Palmate.

*Color.*—Developing leaves, upper surface: Close to 144A. Developing leaves, lower surface: Close to 147B. Fully expanded leaves, upper surface: Between N186A and 187A; venation, close to 187A. Fully expanded leaves, lower surface: Close to N79A; venation, close to N79B.

*Petiole.*—Length: About 10.9 cm. Diameter: About 2.7 mm. Texture, upper and lower surfaces: Smooth, glabrous. Color, upper and lower surfaces: Close to 187A.

Flower description: Flower development has not been observed on plants of the new *Ipomoea*.

Temperature tolerance: Plants of the new *Ipomoea* have been observed to tolerate temperatures from about 5° C. to about 35° C.

Pathogen/pest resistance: Plants of the new *Ipomoea* have not been observed to be resistant to pests and pathogens common to *Ipomoea*.

It is claimed:

1. A new and distinct *Ipomoea* plant named 'Kyuikukan 5' as illustrated and described.

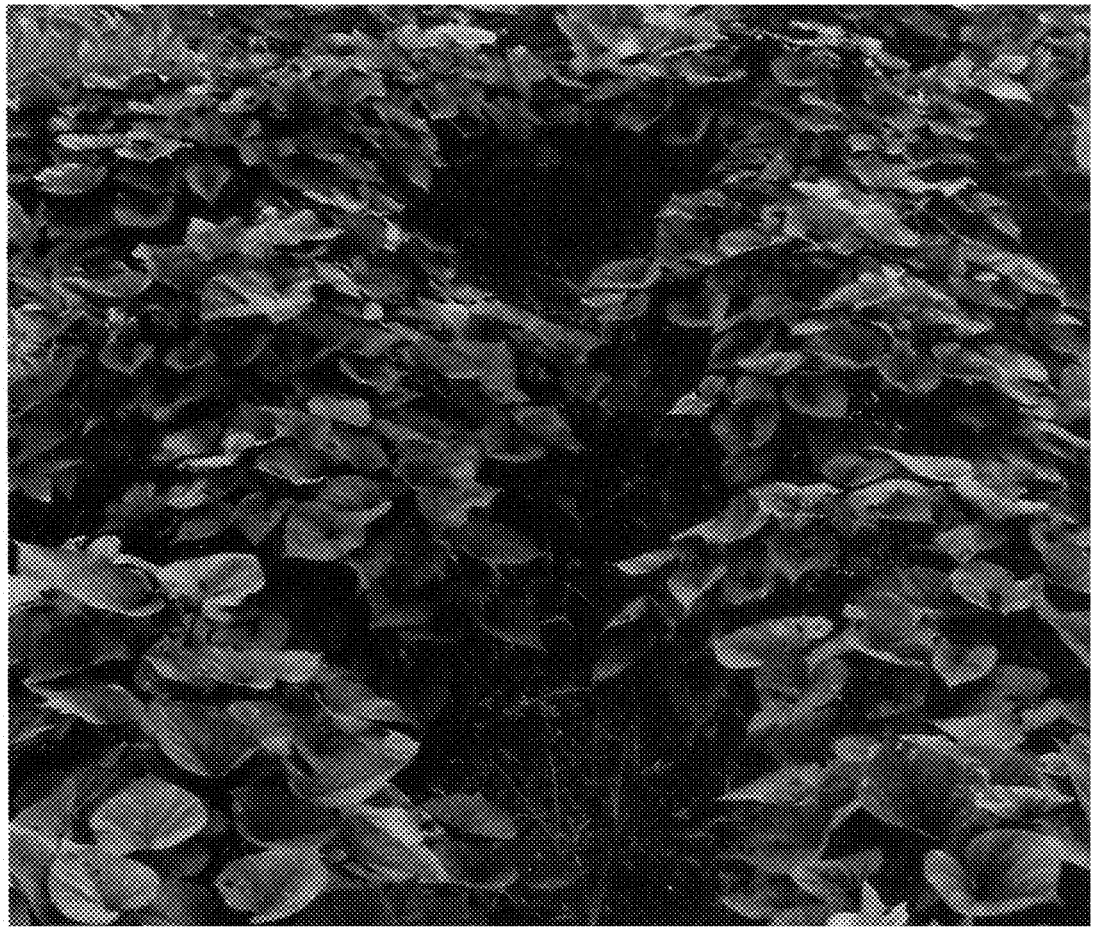

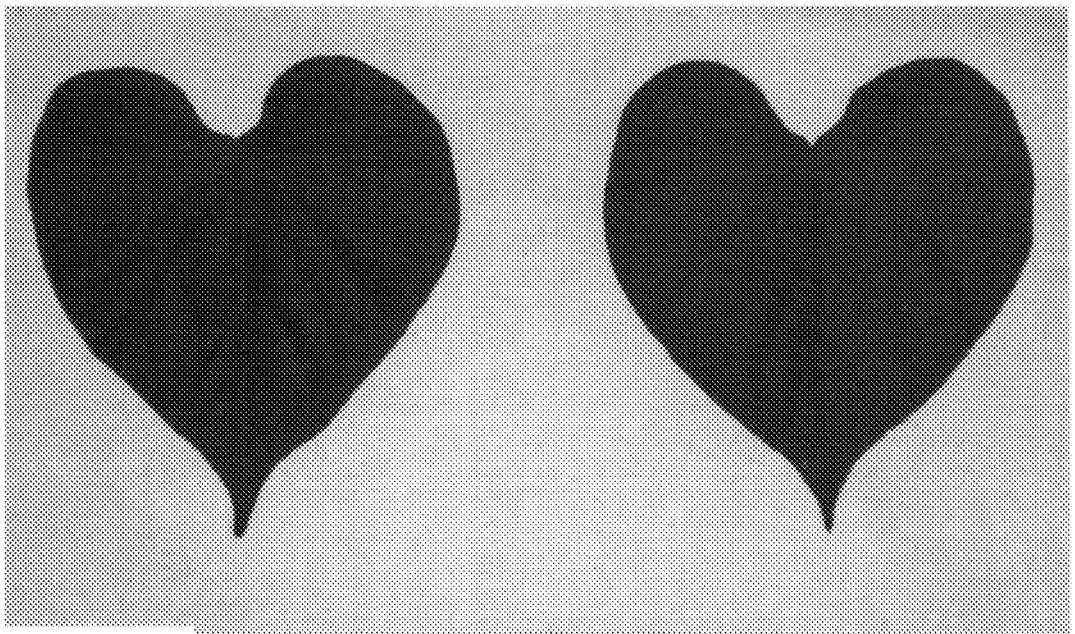
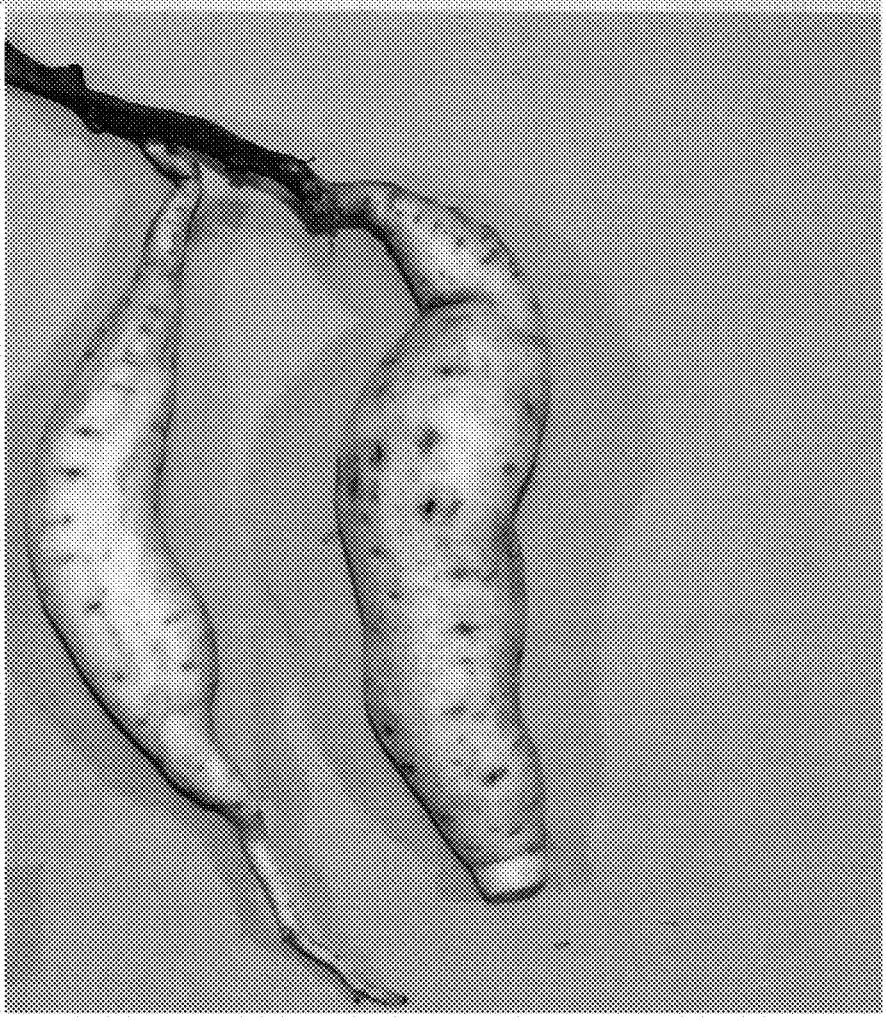

* * * * *